United States Patent
Rezach et al.

(10) Patent No.: US 9,622,788 B2
(45) Date of Patent: Apr. 18, 2017

(54) IMPLANT ASSEMBLY WITH A RIGID INTERFACE

(75) Inventors: William Alan Rezach, Atoka, TN (US); Harold S. Taylor, Memphis, TN (US); Andrew Taylor, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/287,468

(22) Filed: Nov. 2, 2011

(65) Prior Publication Data

US 2013/0110176 A1    May 2, 2013

(51) Int. Cl.
*A61B 17/70* (2006.01)

(52) U.S. Cl.
CPC .......... *A61B 17/7037* (2013.01); *A61B 17/70* (2013.01); *A61B 17/7032* (2013.01); *A61B 17/7038* (2013.01)

(58) Field of Classification Search
CPC ............ A61B 17/7001; A61B 17/7032; A61B 17/7034; A61B 17/7037; A61B 17/7038; A61B 17/84; A61B 17/8033–17/8047
USPC .................................. 606/246–279, 300–321
See application file for complete search history.

(56) References Cited

U.S. PATENT DOCUMENTS

| | | |
|---|---|---|
| 4,261,351 A | 4/1981 | Scherfel |
| 4,463,753 A | 8/1984 | Gustilo |
| 4,569,338 A | 2/1986 | Edwards |
| 4,640,271 A | 2/1987 | Lower |
| 4,756,653 A | 7/1988 | Berger |
| 4,791,918 A | 12/1988 | Von Hasselbach |
| 4,870,957 A | 10/1989 | Goble et al. |
| 2004/0068319 A1* | 4/2004 | Cordaro ..................... 623/17.11 |
| 2004/0204711 A1* | 10/2004 | Jackson ......................... 606/61 |
| 2006/0036242 A1 | 2/2006 | Nilsson |
| 2007/0088357 A1 | 4/2007 | Johnson |
| 2007/0093818 A1* | 4/2007 | Biedermann et al. .......... 606/61 |
| 2007/0233063 A1* | 10/2007 | Rezach ........................... 606/61 |
| 2008/0147129 A1* | 6/2008 | Biedermann et al. ........ 606/308 |
| 2008/0177260 A1 | 7/2008 | Mckinley |
| 2008/0177321 A1 | 7/2008 | Drewry |
| 2008/0312655 A1* | 12/2008 | Kirschman et al. ............ 606/60 |
| 2009/0062866 A1* | 3/2009 | Jackson ........................ 606/301 |

(Continued)

FOREIGN PATENT DOCUMENTS

WO    WO 2010058358 A2 *  5/2010

*Primary Examiner* — Nicholas Plionis (57) ABSTRACT

An implant assembly and a method of assembling the same are provided, the implant assembly including a receiver extending along a central longitudinal axis between a proximal end and an opposite distal end, the receiver including a distal portion defining a receptacle opening at the distal end and a pair of arms extending from the distal portion along the central longitudinal axis on opposite sides of a passage with the passage opening at opposite sides of the receiver, a bone anchor including a distal bone engaging portion and a head at a proximal end of the distal bone engaging portion, the head being positioned in the receptacle with the bone engaging portion in a selected orientation relative to the central longitudinal axis of the receiver and a connector member configured to form a rigid interface between the receiver and the head of the bone anchor thereby providing torque transfer throughout the implant assembly.

20 Claims, 6 Drawing Sheets

(56) References Cited

U.S. PATENT DOCUMENTS

| | | | |
|---|---|---|---|
| 2009/0082809 A1* | 3/2009 | Nguyen et al. | 606/246 |
| 2009/0182384 A1* | 7/2009 | Wilcox et al. | 606/305 |
| 2009/0287249 A1* | 11/2009 | Reynolds et al. | 606/246 |
| 2010/0049255 A1* | 2/2010 | Matthis et al. | 606/279 |
| 2010/0063550 A1* | 3/2010 | Felix et al. | 606/301 |
| 2010/0211114 A1 | 8/2010 | Jackson | |
| 2010/0312279 A1* | 12/2010 | Gephart et al. | 606/264 |
| 2011/0106175 A1 | 5/2011 | Rezach | |

* cited by examiner

IMPLANT ASSEMBLY WITH A RIGID INTERFACE

TECHNICAL FIELD

The present disclosure generally relates to medical devices for the treatment of spinal disorders, and more particularly to an implant assembly having a bone anchor with a rigid interface.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Several techniques and systems have been developed for correcting and stabilizing the spine and for facilitating fusion at various levels of the spine. In one type of system, an elongated rod is disposed longitudinally along the length of the spine or several vertebrae of the spinal column. The rod may be bent to correspond to the normal or desired curvature of the spine in the particular region being instrumented. For example, the rod can be bent or angled to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the lamina of the vertebra. Another type of fixation element is a spinal screw, which can be threaded into various aspects of the vertebral bone, such as the pedicle.

In one typical procedure utilizing a bendable, angled or linear rod, one or more of the rods is situated on one or both of the opposite sides of the spine or spinous processes. A plurality of bone screws is threadingly engaged to several vertebral bodies, such as to the pedicles of these vertebrae. One or more of the bone screws are maneuvered to manipulate the position or orientation of the vertebral body or bodies to which the bone screw is engaged. The rod(s) are connected or affixed to the plurality of bone screws to apply and maintain corrective and stabilizing forces to the spine.

The bone screws or anchors in spinal procedures can have receivers with channels for the elongated rod or other member that, in some bone anchors, open upward, e.g., directly away from the bone to which the anchor is attached. Other bone anchors utilize channels that open along the medial or lateral side of the anchor to receive the rod. Frequently, after implantation, the bone receiver and bone anchor become loose and move in unwanted directions relative to each other and relative to other components of the spinal implant. In some procedures it would therefore be desirable to utilize a bone anchor where the bone anchor interface with the receiver is fixed relative to one another so that the forces applied to the receiver are effectively transferred to the vertebrae.

SUMMARY

Accordingly, a bone anchor is provided including a receiver extending along a central longitudinal axis between a proximal end and an opposite distal end, the receiver including a distal portion defining a receptacle opening at the distal end and a pair of arms extending from the distal portion along the central longitudinal axis on opposite sides of a passage with the passage opening at opposite sides of the receiver, the receiver including a bottom surface extending along the passage between the pair of arms, wherein the receptacle opens into the passage through the bottom surface. The bone anchor also includes a bone anchor having a distal bone engaging portion and a head at a proximal end of the distal bone engaging portion, the head being positioned in the receptacle with the bone engaging portion in a selected orientation relative to the central longitudinal axis of the receiver and a connector or retaining member configured to form a rigid interface between the receiver and the head of the bone anchor thereby providing torque transfer throughout the implant assembly. The rigid interface is obtained by fusing the connector or retaining member to the head of the bone anchor. As examples, the fusing could be induced by laser welding, TIG welding or MIG welding.

In another embodiment, the head of the bone anchor further defines at least one detent in a threaded portion thereof. The opposite distal end of the receiver of the implant assembly further defines at least one aperture adjacent a distal side portion of the receiver, wherein the aperture is configured for alignment with the detent of the head of the bone anchor. The implant assembly also includes at least a cross pin extending through the at least one aperture of the receiver into the at least one detent of the bone anchor thereby forming a rigid interface between the receiver and the bone anchor.

According to another aspect, the head of the bone anchor further defines at least one detent in a threaded portion thereof. The opposite distal end of the receiver of the implant assembly further defines at least one aperture adjacent a distal side portion of the receiver, the aperture configured for alignment with the detent of the head of the bone anchor. The implant assembly also includes a medical grade threadlocker adhesive, which can be inserted into the aperture of the head of the receiver, thereby forming a rigid interface between the receiver and the bone anchor.

In yet another embodiment the implant assembly further includes an engaging member engaged to the pair of arms to secure a connecting element, for example, an intervertebral rod, against the proximal support surface of the saddle, wherein the saddle engages the receiver and is limited to movement in the receiver in a single plane defined by the central longitudinal axis of the receiver and the central longitudinal axis of the connecting element while the bone engaging portion remains in the selected orientation.

In yet another aspect, a implant assembly is provided including a receiver extending along a central longitudinal axis between a proximal end and an opposite distal end, the receiver including a distal portion defining a receptacle opening at the distal end and a pair of arms extending from the distal portion along the central longitudinal axis on opposite sides of a passage with the passage opening at opposite sides of the receiver, the receiver including a bottom surface extending along the passage between the pair of arms, wherein the receptacle opens into the passage through the bottom surface. The implant assembly also includes a bone anchor including a distal bone engaging portion and a head at a proximal end of the distal bone engaging portion, the head being positioned in the receptacle with the bone engaging portion in a selected orientation relative to the central longitudinal axis of the receiver. The implant assembly also contains a rigid interface formed between the receiver and the bone anchor, the interface configured for torque transfer throughout the implant assembly, wherein the rigid interface is formed by crimping the receiver over the bone anchor.

In another embodiment, the implant assembly can be assembled according to the following steps: providing a receiver extending along a central longitudinal axis between a proximal end and an opposite distal end, the receiver including a distal portion defining a receptacle opening at the distal end and a pair of arms extending from the distal portion along the central longitudinal axis on opposite sides of a passage with the passage opening at opposite sides of the receiver, the receiver including a bottom surface extending along the passage between the pair of arms, wherein the receptacle opens into the passage through the bottom surface; providing a saddle and positioning the saddle in the passage of the receiver adjacent to the bottom surface of the receiver; providing a connector member and placing the connector member into the receptacle of the receiver adjacent the saddle; providing a bone anchor including a distal bone engaging portion and a head at a proximal end of the distal bone engaging portion, threading the head of the bone anchor into the connector member; and forming a rigid interface between the receiver and the head of the bone anchor thereby providing torque transfer throughout the implant assembly.

In yet another embodiment, another method for assembling a implant assembly includes providing a receiver extending along a central longitudinal axis between a proximal end and an opposite distal end, the receiver including a distal portion defining a receptacle opening at the distal end and a pair of arms extending from the distal portion along the central longitudinal axis on opposite sides of a passage with the passage opening at opposite sides of the receiver, the receiver including a bottom surface extending along the passage between the pair of arms, wherein the receptacle opens into the passage through the bottom surface. The method also includes providing a saddle and positioning the saddle in the passage of the receiver adjacent to the bottom surface of the receiver, providing a bone anchor including a distal bone engaging portion and a head at a proximal end of the distal bone engaging portion, threading the head of the bone anchor into the receiver; and crimping the receiver over the head of the bone anchor thereby forming a rigid interface between the receiver and the head of the bone anchor and providing a torque transfer throughout the implant assembly.

BRIEF DESCRIPTION OF THE DRAWINGS

The present disclosure will become more readily apparent from the specific description accompanied by the following drawings, in which.

Like reference numerals indicate similar parts throughout the figures. It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

The exemplary embodiments of the vertebral rod system and methods of use disclosed are discussed in terms of medical devices for the treatment of spinal disorders and more particularly, in terms of a implant assembly for delivery to a surgical site. It is envisioned that the implant assembly and methods of use disclosed provide stability and maintain structural integrity while reducing stress on spinal elements.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is further envisioned that the present disclosure may be employed with surgical treatments including open surgery and minimally invasive procedures, of such disorders, such as, for example, discectomy, laminectomy, fusion, bone graft and implantable prosthetics. It is contemplated that the present disclosure may be employed with other osteal and bone related applications, including those associated with diagnostics and therapeutics. It is further contemplated that the disclosed implant assembly may be employed in a surgical treatment with a patient in a prone or supine position, employing a posterior, lateral or anterior approach. The present disclosure may be employed with procedures for treating the lumbar, cervical, thoracic and pelvic regions of a spinal column.

The present disclosure may be understood more readily by reference to the following detailed description taken in connection with the accompanying drawing figures, which also form a part of this disclosure. It is to be understood that this disclosures is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The following discussion includes a description of a implant assembly, related components and exemplary methods of employing the implant assembly in accordance with the principles of the present disclosure. Alternate embodiments are also disclosed. Reference will now be made in detail to the exemplary embodiments of the present disclosure, which are illustrated in the accompanying figures. Turning now to FIGS. 1 to 4B, there are illustrated components of a implant assembly in accordance with the principles of the present disclosure.

Figure 1:
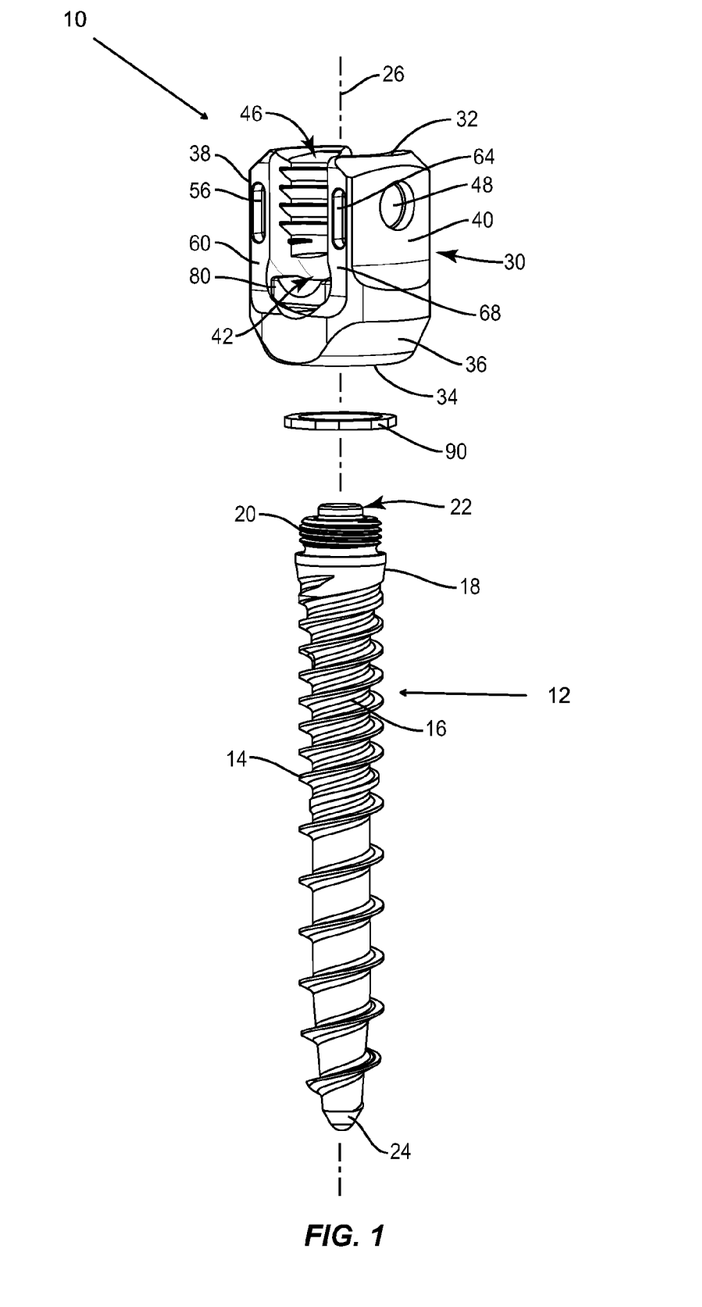
FIG. 1 is a perspective view of one particular embodiment of the implant assembly in accordance with the principles of the present disclosure.

With reference to FIG. 1, in an embodiment, there is provided a implant assembly 10 including a bone anchor 12 and a receiver 30. The bone anchor includes a proximal head 20, a threaded bone engaging portion 14 configured as a bone screw, vertebral hook, bone clamp and/or other suitable bone engaging arrangement. The elongated bone engaging portion 14 extends from a distal end portion 24 to proximal head 20 that is centered on a central longitudinal axis 26. Bone engaging portion 14 is elongated and has at least one or more threads along at least a portion thereof. The threads of bone engaging portion 14 may be self-tapping, self-drilling, continuous, intermittent, of multiple thread forms, or other appropriate configurations, wherein the threads may be closer or further apart. The diameter of the bone engaging portion 14 can preferably be in the range of about 4 mm to about 12.5 mm in diameter and a length that can vary from about 30 mm to about 140 mm.

Figure 1A:
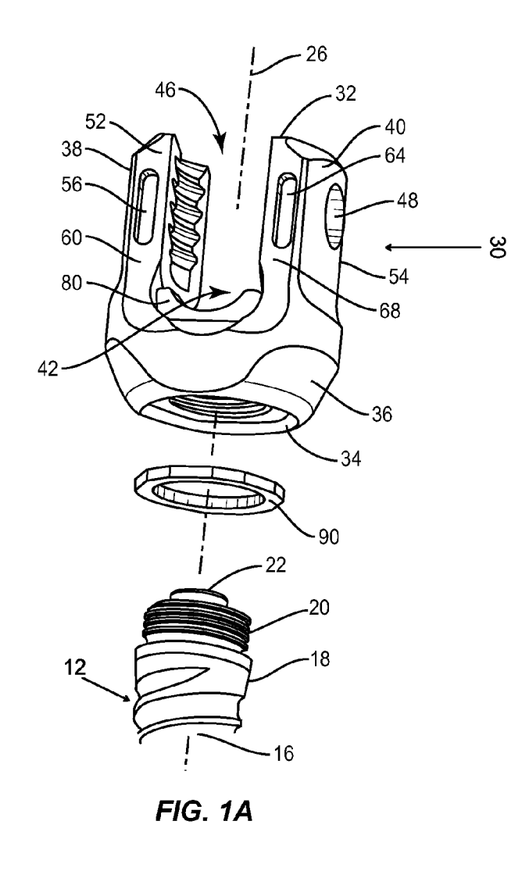
FIG. 1A is a perspective view of the implant assembly shown in FIG. 1.
Figure 1B:
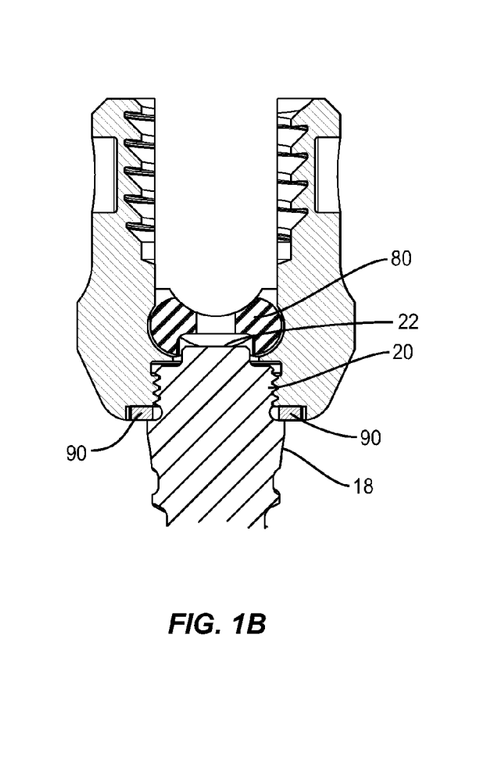
FIG. 1B is a section view along the longitudinal axis of the implant assembly shown in FIG. 1A.

Referring to FIG. 1, 1A or 1B, proximal head 20 of bone anchor 12 has a threaded circular shape configured to fit into receiver 30. The threaded portion is further capped by a circular platform 22. The elongated bone engaging portion 14 also contains a shaft 16 and a transition portion 18, which extends between shaft 16 and proximal head 20 of bone anchor 12. The threaded portion of the shaft 16 includes helical threads, which can be spaced closer together next to the transition portion 18 but further apart closer to distal end 24.

In one embodiment, implant assembly 10 includes receiver 30 configured to couple to bone anchor 12 through retaining member 90. Receiver 30 includes a U-shaped body extending along central longitudinal axis 26 between proximal end 32 and distal end 34. The U-shaped body can be any shape including, tulip shape, square, rectangular, oval, circular, or the like. Receiver 30 includes a distal bowl portion 36 and a pair of arms 38 and 40 extending proximally from distal bowl 36 on opposite sides of longitudinal axis 26 to proximal end 32. Arms 38, 40 define passage 42 therebetween that opens at opposite sides of arms 38, 40 to receive an elongated intervertebral member such as a rod (not shown) in a transverse position to longitudinal axis 26. Bowl portion 36 defines a receptacle (not shown) that opens into passage 42 and extends from passage 42 through distal end 34. Arms 38 and 40 also define a proximal opening 46 at proximal end 32, opening 46 extending along arms 38, 40 to passage 42 that can hold a rod.

Arms 38, 40 each include a circular recess 48 in the outer side surface 52, 54, respectively, thereof that face opposite directions from one another. Arm 38 also includes oblong recesses 56 in each of the opposite end surfaces 60 thereof. Arm 40 similarly includes oblong recesses 64 in each of the opposite end surfaces 68 thereof. The recesses provide locations in which various tools and instrumentation can be engaged and mounted to receiver 30 to facilitate implantation and maneuvering of bone anchor 12 and a connecting element such as intervertebral rod in the patient.

Receiver 30 also includes a bottom surface that extends between inner surfaces of arms 38, 40 along distal side of passage 42. The bottom surface of receiver 30 is configured to accept saddle 80. Saddle 80 is positioned in receiver 30 between an elongated member such as an intervertebral rod and head 20 of bone anchor 12. A useful configuration of saddle 80 has been described in U.S. Ser. No. 12/609,906, the content of which is hereby incorporated by reference herein as if set forth in full.

As further illustrated in FIGS. 1, 1A and 1B, the implant assembly also includes retaining member 90, which in a preferred embodiment is a washer configured to couple bone anchor 12 to receiver 30. The washer can, in some embodiments, be a keyed washer having a tab or projection or recess that allows the washer to slide along the longitudinal axis and, in some embodiments, not rotate along it. The keyed washer can be configured to fit or slide over the transition portion 18 of the bone anchor 12, proximal head 20, circular platform 22, and/or fit or slide within the receiver 30. In this way, the washer provides a rigid interface between the bone anchor and the receiver. The washer can be any shape including, oval, oblong, triangular, rectangular, square, polygonal, irregular, tubular, non-tubular, uniform, non-uniform, variable and/or tapered in shape.

The bone anchor and/or receiver, in some embodiments, may be configured to receive and/or mate with the washer or keyed washer and lock the washer, bone anchor, and or receiver into place. In some embodiments, retaining member 90 can be placed around transition portion 18 of bone anchor 12. In a preferred embodiment, retaining member 90 and bone anchor 12 are manufactured from the same material, preferably an implant grade titanium alloy, such as for example, Ti-6AI-4V.

In a preferred embodiment, the implant assembly is assembled by inserting saddle 80 into receiver 30 such that saddle 80 can pivot therein and retaining member 90 is inserted into receiver 30. Bone anchor 12 is then threaded into receiver 30 by applying a torque from about 6.7 Nm to about 9.4 Nm. Retaining member 90 is then laser welded onto receiver 30 such that the welded area is capable of resisting a torque of about 90 in-lbs or 10.2 Nm thereby obtaining a rigid connection between receiver 30 and bone anchor 12 capable of torque transferring throughout the implant assembly.

The welding of retaining member 90 to receiver 30 can also be accomplished by MIG or TIG welding. As used herein, MIG welding refers to a gas metal arc welding procedure wherein a metal wire is continuously fed from a spool and the primary shielding gas is selected from argon, a mixture of argon and oxygen, a mixture of argon and carbon dioxide or a mixture or argon and helium. As used herein TIG welding refers to gas tungsten arc welding wherein an arc is formed between a nonconsumable tungsten electrode and the metal being welded. Shielding gases include argon, argon hydrogen mixture and argon helium mixture.

Figure 2:
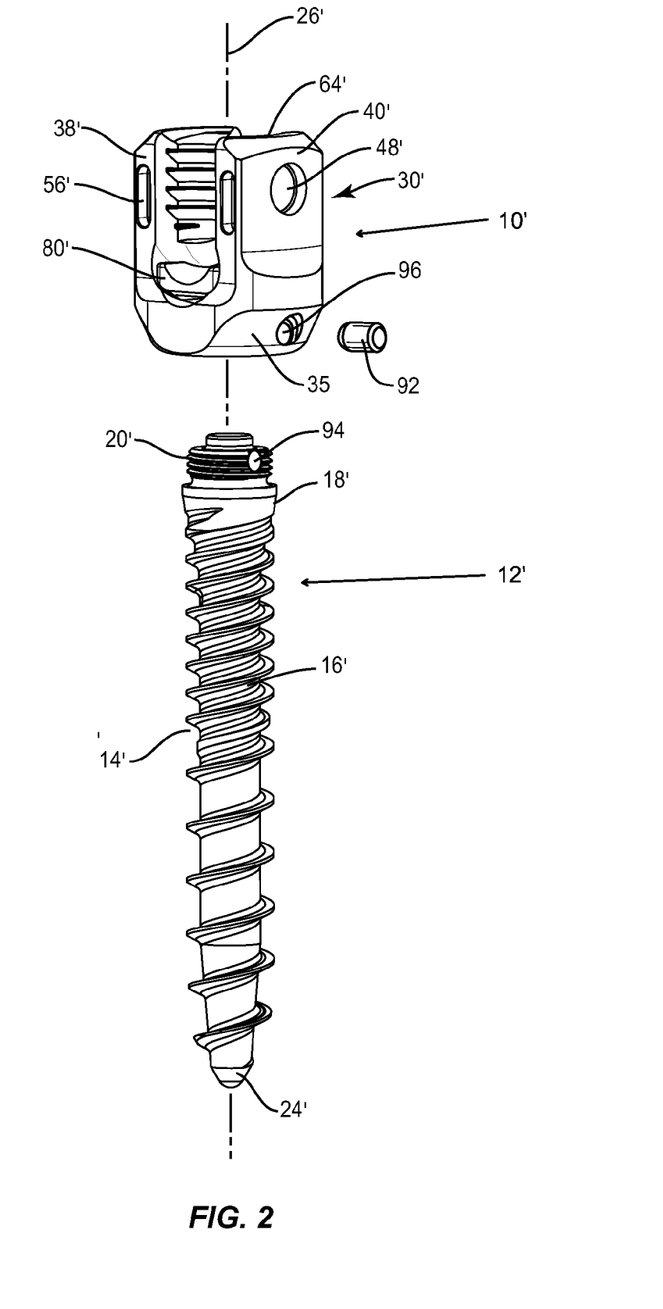
FIG. 2 is a perspective view of another particular embodiment of the implant assembly in accordance with the principles of the present disclosure.
Figure 2A:
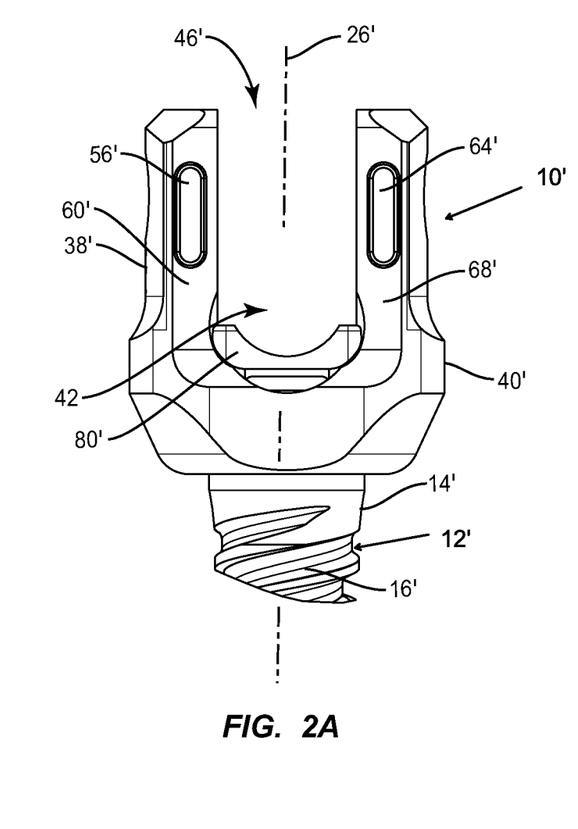
FIG. 2A is a perspective view of the implant assembly shown in FIG. 2.
Figure 2B:
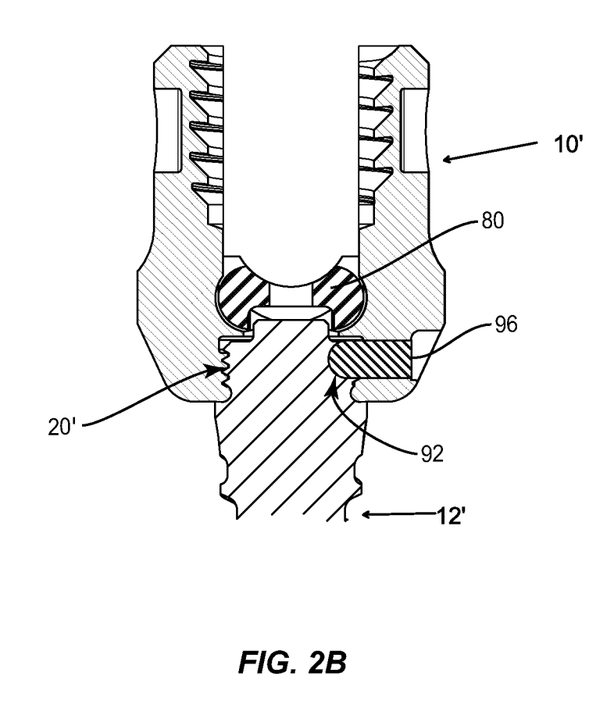
FIG. 2B is a section view along the longitudinal axis of the implant assembly shown in FIG. 2A.

Referring now to FIGS. 2, 2A and 2B, implant assembly 10' is similar to implant assembly 10, but includes another type of retaining member for securing receiver 30' to bone anchor 12'. Bone anchor 12' includes a proximal head 20' having at least one detent (only one detent is shown in FIGS. 1, 1A and 1B) 94 formed in the threaded portion of proximal head 20' of bone anchor 12'. Receiver 30' includes opposite aperture 96 adjacent the distal side thereof that aligns with respective detent 94. A cross pin 92 is positioned in aperture 96 and detent 94. Cross pin 92 pivotally couples receiver 30' to head 20' to limit pivoting of receiver 30' to pivoting movement around cross pin 92 in the plane defined by the longitudinal axis 26' of receiver 30'. Cross pin 92 defines a pivot axis that is orthogonal to longitudinal axis 26' of receiver 30'. Similar to the embodiment where the retaining member is a washer, in this embodiment where the retaining member is a cross pin, cross pin 92 and bone anchor 12' are manufactured from the same material, preferably an implant grade titanium alloy. In some embodiments, the receiver can be manufactured from the same or different material as the cross pin and/or bone anchor. In some embodiments, the cross pin can be used in combination with a washer.

In a preferred embodiment, the implant assembly is assembled by inserting saddle 80' into receiver 30' such that saddle 80' can pivot therein; thereafter, head 20' of bone anchor 12' is threaded into receiver 30' by applying a torque from about 6.7 Nm to about 9.4 Nm. Cross pin 92 is then pressed through aperture 96 to lock bone anchor 12' and receiver 30'. Thereafter cross pin 92 is laser welded onto receiver 30' such that the welded cross pin is capable of resisting a torque of about 4.5 Nm thereby obtaining a rigid connection between receiver 30' and bone anchor 12'. The welding of cross pin 92 to receiver 30' can also be accomplished by laser, MIG or TIG welding as described above in connection with another embodiment when the retaining member is a washer. In some embodiments, the cross pin can be inserted to contact a surface of the bone anchor without the need for welding.

Arms 38', 40' each include a circular recess 48' in the outer side surface thereof that face opposite directions from one another. Arm 38' also includes oblong recesses 56' in each of the opposite end surfaces 60' and 68'. Arm 40' similarly includes oblong recesses 64' in each of the opposite end surfaces thereof. The recesses provide locations in which various tools and instrumentation can be engaged and mounted to receiver 30' to facilitate implantation and maneuvering of bone anchor 12' and a connecting element such as intervertebral rod in the patient. The receiver can also have portion 35 for engaging the bone anchor 12'.

In some embodiments, the bone anchor 12' comprises proximal head 20' of bone anchor 12' that has a threaded circular shape configured to fit into receiver 30'. The proximal head is configured to receive and be held in position by cross pin 92. In some embodiments, the cross pin 92 can deform the threaded portion of the bone anchor 12' so that the receiver 30' can remain in position and the cross pin 92 will create a rigid interface between the receiver 30' and the bone anchor 12'. The elongated bone engaging portion 14' of the bone anchor 12' also contains a shaft 16' and a transition portion 18' which extends between shaft 16' and proximal head 20' of bone anchor 12'. The threaded portion of the shaft 16' includes helical threads which can be spaced closer together next to the transition portion 18' but further apart closer to distal end 24'.

Figure 3:
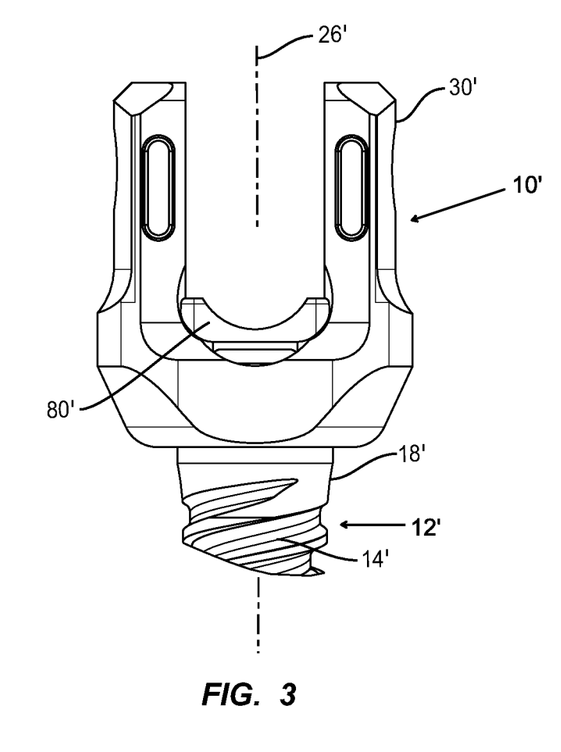
FIG. 3 is a perspective view of another particular embodiment of the implant assembly in accordance with the principles of the present disclosure.
Figure 3A:
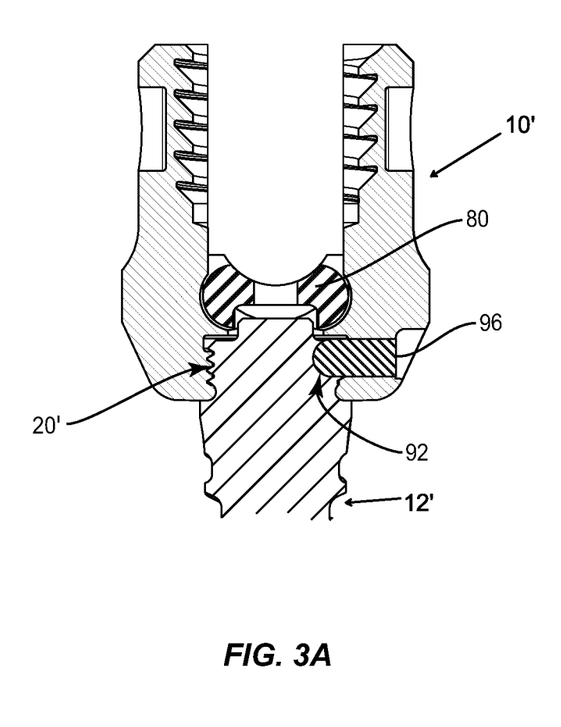
FIG. 3A is section view along the longitudinal axis of the implant assembly shown in FIG. 2A.

In another embodiment, as illustrated in FIGS. 3 and 3A, aperture 96 is not fitted with a cross pin, instead it is filled with a biocompatible, medical grade threadlocker adhesive such as available from Loctite®, 3M® or Ellsworth®. As a result, the biocompatible adhesive forms a rigid connection between receiver 30' and bone anchor 12'. In some embodiments, the adhesive can be cured about the threads of the bone fastener and/or receiver.

Figure 4:
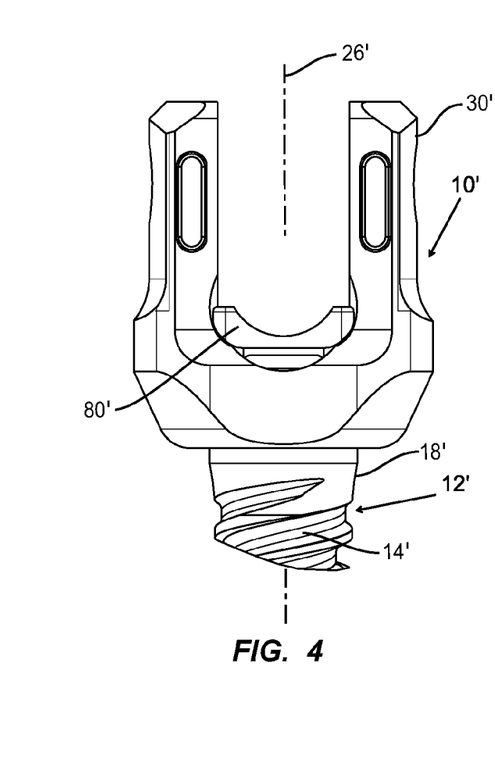
FIG. 4 is a perspective view of another particular embodiment of the implant assembly in accordance with the principles of the present disclosure.
Figure 4A:
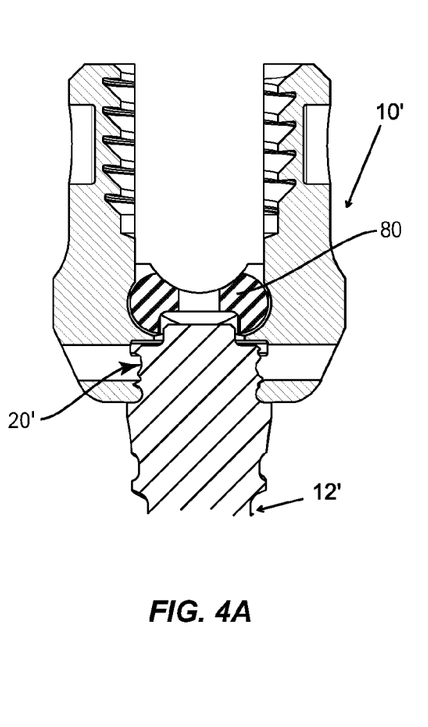
FIG. 4A is a section view along the longitudinal axis of the implant assembly shown in FIG. 2A.
Figure 4B:
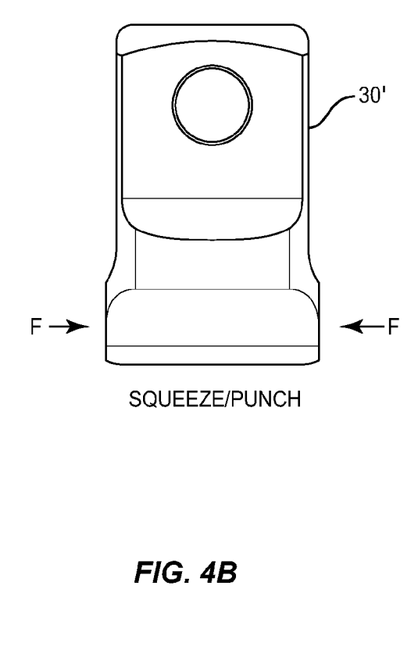
FIG. 4B is a schematic of a method of crimping the receiver around the bone anchor of the implant assembly shown in FIG. 4A.

As illustrated in FIGS. 4, 4A and 4B, in yet another aspect, the implant assembly 10' a rigid connection between receiver 30' and bone anchor 12' is attained by connecting receiver 30' and the bone anchor 12' with a crimping operation akin to a squeeze and punch peration of receiver 30' around head 20' of bone anchor 12' is performed wherein the threaded interface between head 20' and receiver 30' is mashed into one rigid connection capable of torque transfer over the transition portion 18' of the bone anchor 12'. This crimping functions to deform the threads of the bone anchor and/or receiver and cause a rigid interface between the receiver and the bone anchor. In some embodiments, the implant assembly provides a mono-axial type of assembly and, in some embodiments, can be used with tulip style or side loading style rod receivers. In some embodiments, the implant assembly may comprise indicator markings (e.g., numbers, lines, letters, radiographic markers, etc.) disposed on the body, distal and/or proximal end of the bone anchor or the receiver to indicate position of the receiver and/or bone anchor. In some embodiment, the marker can be disposed on the head of the bone anchor to indicate that the receiver has been compressed onto the head of the bone anchor.

In this embodiment shown in FIGS. 4, 4A and 4B, there is no need for a glue or washer. In the embodiment shown, the implant assembly 10' is assembled by inserting saddle 80' into receiver 30' such that saddle 80' can pivot therein; thereafter, head 20' of bone anchor 12' is threaded into receiver 30' by applying a torque from, for example, about 6.7 Nm to about 9.4 Nm and then application of a crimping process.

Materials for the anchors, receivers, saddles and engaging members disclosed herein can be chosen from any suitable biocompatible material, such as titanium, titanium alloys, cobalt-chromium, cobalt-chromium alloys, or other suitable metal or non-metal material. Connector or retaining member 90 can be made from the same material as one or more of the components of the anchor assembly to which it is engaged, or from a different material. For example, connector or retaining member 90 can be made from PEEK, plastic, titanium or titanium alloy, cobalt-chrome, composite material, or other material that is the same or different from the material of one or more components of the anchor assembly to which is engaged. The anchor assemblies can be sized for placement at any level of the spine and for engagement with any bony portion of the spine. In one particular embodiment, the anchor assemblies are engaged to pedicles of the vertebrae. Of course, it is understood that the relative size of the components of the anchor assemblies can be modified for the particular vertebra(e) to be instrumented and for the particular location or structure of the vertebrae to which the anchor assembly will be engaged.

In some embodiments, a method of assembling the implant assembly is provided where the implant assembly can be assembled by placing the washer on the head and/or shaft of the bone anchor, then placing the receiver on the head and/or shaft of the bone anchor and applying a turning force or torque to the receiver to cause the washer to create a rigid interface between the receiver and the head and/or shaft of the bone anchor so the fit is tight and there is little or no motion of the components. The washer can also be welded to the device.

In some embodiments, a method of assembling the implant assembly is provided where the implant assembly can be assembled by placing the receiver on the head and/or shaft of the bone anchor and inserting a cross pin into the receiver to cause a rigid interface between the receiver and the head and/or shaft of the bone anchor so the fit is tight and there is little or no motion of the components. The pin can also be welded or glued to the bone anchor and/or receiver.

In some embodiments, a method of assembling the implant assembly is provided where the implant assembly can be assembled by placing the receiver on the head and/or shaft of the bone anchor and compressing or crimping the receiver onto the head and/or shaft of the bone anchor to cause a rigid interface thereto so the fit is tight and there is little or no motion of the components.

In some embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in some embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the device, including, but not limited to, gas sterilization, such as, for example, with ethylene oxide or steam sterilization.

In some embodiments, a kit is provided which may include additional parts along with the implant assembly device combined together to be used for implantation. The kit may include the implant assembly device in a first compartment. The second compartment may include any other instruments needed for the surgery. A third compartment may include gloves, drapes, wound dressings and other procedural supplies for maintaining sterility of the implant assembly, as well as an instruction booklet. A fourth compartment may include cannulas and/or needles. Each tool may be separately packaged in a plastic pouch that is radiation sterilized. A cover of the kit may include illustrations of methods of using the implant assembly and a clear plastic cover may be placed over the compartments to maintain sterility.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant assembly comprising:
a receiver extending along a longitudinal axis between a proximal end and a distal end, the proximal end configured for receiving an elongated member, the distal end comprising a threaded inner surface defining a cylindrical shaped opening that receives a correspondingly shaped threaded head of a bone anchor such that the threads on the inner surface engage the threads on the head, the bone anchor having a tip opposite the head, the tip configured to engage bone, a connector member that contacts at least the distal end of the receiver and at least the head of the bone anchor to provide a rigid interface between the receiver and the head of the bone anchor such that the receiver is fixed relative to the bone anchor, the assembly further comprising a saddle, separate from the connector member, inserted into the receiver such that the saddle can pivot therein.

2. An implant assembly of claim 1, wherein:
the receiver comprises a first aperture extending perpendicular to the longitudinal axis;
the head comprises a second aperture extending perpendicular to the longitudinal axis, the first and second apertures being coaxial when the threads on the inner surface engage the threads on the head; and
the connector member comprises a cross pin that extends through the first aperture and the second aperture to form the rigid interface.

3. An implant assembly of claim 1, wherein the rigid interface is formed by fusing the connector member to the head of the bone anchor.

4. An implant assembly according to claim 3, wherein the fusing is induced by laser welding, TIG welding or MIG welding.

5. An implant assembly of claim 1, wherein the connector member is a washer that has a keyed outer surface that engages the receiver such that relative rotation between the washer and the receiver is resisted.

6. An implant assembly of claim 1, wherein the bone anchor includes an annular flange positioned between the head and the tip that engages a distal end surface of the receiver when the threads on the inner surface engage the threads on the head to prevent the receiver from translating distally relative to the bone anchor along the longitudinal axis.

7. An implant assembly of claim 1, wherein the implant assembly provides a mono-axial type of assembly.

8. An implant assembly of claim 1, wherein:
the connector member is a washer;
the bone anchor includes an annular flange positioned between the head and the tip and the receiver comprises a cutout that is distal to the cylindrical shaped opening; and
the washer is positioned within the cutout such that a distal surface of the washer engages the annular flange.

9. An implant assembly of claim 1, wherein:
the connector member is a washer; and
the washer is not supported by the receiver.

10. An implant assembly of claim 1, wherein the saddle is spaced apart from the connector member.

11. An implant assembly of claim 1, wherein an outer surface of the saddle engages an inner surface of the receiver to space the saddle apart from the head.

12. An implant assembly comprising:
a monolithic receiver extending along a central longitudinal axis between a proximal end and an opposite distal end, the receiver including a distal portion comprising a threaded inner surface defining a cylindrical shaped receptacle opening at the distal end and a pair of arms extending from the distal portion along the central longitudinal axis on opposite sides of a passage with the passage opening at opposite sides of the receiver, the receiver including a bottom surface extending along the passage between the pair of arms, wherein the receptacle opens into the passage through the bottom surface;

a bone anchor including a distal bone engaging portion and a threaded cylindrical shaped head at a proximal end of the bone engaging portion, the head being positioned in the receptacle such that the threads on the inner surface engage the threads on the head;

a connector member configured to form a rigid interface between the receiver and the head of the bone anchor such that the receiver is fixed relative to the bone anchor; and a saddle, separate from the connector member, positioned in the passage of the receiver adjacent to a bottom surface of the receiver, the saddle including a proximal support surface and a distal surface opposite the proximal support surface.

13. An implant assembly of claim 12, wherein the connector member is a washer or a cross pin.

14. An implant assembly of claim 12, wherein the rigid interface is formed by fusing the connector member to the head of the bone anchor.

15. An implant assembly of claim 12, wherein the rigid interface is formed by subjecting the connector member to laser welding, TIG welding or MIG welding to the head of the bone anchor.

16. An implant assembly of claim 12, wherein the head of the bone anchor further defines at least one detent in a threaded portion thereof that extends perpendicular to the central longitudinal axis, the opposite distal end of the receiver further defines at least one aperture adjacent a distal side portion of the receiver that extends perpendicular to the central longitudinal axis, the aperture configured for alignment with the detent of the head of the bone anchor, and at least a cross pin extending through the at least one aperture of the receiver into the at least one detent of the bone anchor thereby forming a rigid interface between the receiver and the bone anchor.

17. An implant assembly of claim 12, wherein the head of the bone anchor further defines at least one detent in a threaded portion thereof, the opposite distal end of the receiver further defines at least one aperture adjacent a distal side portion of the receiver, the aperture configured for alignment with the detent of the head of the bone anchor, and a medical grade threadlocker adhesive, the threadlocker adhesive insertable into the aperture of the receiver, thereby forming a rigid interface between the receiver and the bone anchor.

18. An implant assembly of claim 12, wherein the receiver and the bone anchor are manufactured from different materials from one another and the connector member and the bone anchor are manufactured of the same material selected from the group consisting of titanium alloy, cobalt-chrome-molybdenum alloy and other biologically compatible composite materials.

19. An implant assembly of claim 12, further comprising an engaging member engaged to the pair of arms to secure a connecting element against the proximal support surface of the saddle, wherein the saddle engages the receiver and is limited to movement in the receiver about the central longitudinal axis of the receiver.

20. An implant assembly of claim 12, further comprising a marker disposed on the implant assembly for indicating a position of the implant assembly.

\* \* \* \* \*